US012678257B2

(12) United States Patent (10) Patent No.: US 12,678,257 B2
Lim et al. (45) Date of Patent: Jul. 14, 2026

(54) STONE MEASUREMENT SYSTEMS AND METHODS RELATED THERETO

(71) Applicant: Boston Scientific Scimed, Inc., Maple Grove, MN (US)

(72) Inventors: Kian S. Lim, Shrewsbury, MA (US); Longquan Chen, Lexington, MA (US); Niraj Prasad Rauniyar, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 383 days.

(21) Appl. No.: 18/329,157

(22) Filed: Jun. 5, 2023

(65) Prior Publication Data

US 2023/0390019 A1 Dec. 7, 2023

Related U.S. Application Data

(60) Provisional application No. 63/365,900, filed on Jun. 6, 2022.

(51) Int. Cl.
*A61B 90/00* (2016.01)
*A61B 1/07* (2006.01)
(Continued)

(52) U.S. Cl.
CPC ................ *A61B 90/06* (2016.02); *A61B 1/07* (2013.01); *A61B 18/26* (2013.01); *G06T 7/70* (2017.01);
(Continued)

(58) Field of Classification Search
None
See application file for complete search history.

(56) References Cited

U.S. PATENT DOCUMENTS

| | | | | | |
|---|---|---|---|---|---|
| 3,817,631 | A | * | 6/1974 | Kawahara | .......... A61B 1/00177 356/9 |
| 4,660,982 | A | * | 4/1987 | Okada | .................. A61B 1/0615 356/636 |

(Continued)

FOREIGN PATENT DOCUMENTS

| | | | | | |
|---|---|---|---|---|---|
| CN | | 104146711 A | * 11/2014 | ......... A61B 1/00045 |
| DE | | 3629435 A1 | 3/1987 | |

(Continued)

OTHER PUBLICATIONS

International Search Report and Written Opinion in PCT/US2023/024414, dated Sep. 4, 2023 (9 pages).

*Primary Examiner* — John P Leubecker
(74) *Attorney, Agent, or Firm* — Bookoff McAndrews PLLC

(57) ABSTRACT

Medical systems are described, including a medical system that includes a scope including a handle and a shaft defining a channel having a distal opening, a processor, at least one laser source, a first laser fiber, and a second laser fiber, wherein each of the first laser fiber and the second laser fiber is coupled to the at least one laser source and extends through the shaft, wherein a distal end of the shaft includes an imager, the distal opening of the channel, a distal end of the first laser fiber, and a distal end of the second laser fiber, and wherein each of the first laser fiber and the second laser fiber is configured to transmit a collimated beam onto a target without altering or fragmenting the target.

17 Claims, 5 Drawing Sheets

(51) Int. Cl.
    *A61B 18/00*        (2006.01)
    *A61B 18/26*        (2006.01)
    *G06T 7/70*         (2017.01)

(52) U.S. Cl.
    CPC ............... *A61B 2018/00511* (2013.01); *A61B 2090/061* (2016.02); *G06T 2207/10068* (2013.01)

(56)            References Cited

U.S. PATENT DOCUMENTS

| | | | | |
|---|---|---|---|---|
| 8,827,896 | B2* | 9/2014 | Tsuruta ............... | A61B 1/00009 |
| | | | | 600/109 |
| 9,113,822 | B2* | 8/2015 | Sharonov ........... | A61B 1/00131 |
| 11,536,556 | B2* | 12/2022 | Sonoda ................... | A61B 5/064 |
| 2004/0242961 | A1* | 12/2004 | Bughici ............. | G02B 23/2469 |
| | | | | 356/610 |
| 2006/0204953 | A1* | 9/2006 | Ptitsyn .................. | G06T 7/0012 |
| | | | | 382/128 |
| 2007/0139953 | A1* | 6/2007 | Krattiger ................ | A61B 1/042 |
| | | | | 362/574 |
| 2007/0161854 | A1* | 7/2007 | Alamaro .............. | A61B 1/0676 |
| | | | | 600/109 |
| 2007/0225559 | A1* | 9/2007 | Clerc ..................... | A61B 1/018 |
| | | | | 600/113 |
| 2009/0097725 | A1* | 4/2009 | Krupnik ................. | A61B 1/041 |
| | | | | 382/128 |
| 2009/0189972 | A1* | 7/2009 | Harris .................... | A61B 5/444 |
| | | | | 348/14.08 |
| 2009/0318760 | A1* | 12/2009 | Pascal ................. | A61B 1/0607 |
| | | | | 600/117 |
| 2010/0324366 | A1* | 12/2010 | Shimotsu ............... | A61B 1/045 |
| | | | | 600/109 |
| 2013/0027548 | A1* | 1/2013 | Gere .................... | H04N 5/2226 |
| | | | | 348/140 |
| 2013/0194404 | A1* | 8/2013 | Christiansen ...... | A61B 1/00188 |
| | | | | 348/67 |
| 2013/0296712 | A1* | 11/2013 | Durvasula ................ | A61B 1/06 |
| | | | | 600/477 |
| 2014/0031665 | A1* | 1/2014 | Pinto ...................... | A61B 90/06 |
| | | | | 600/407 |
| 2015/0161802 | A1* | 6/2015 | Christiansen ........ | A61B 5/1076 |
| | | | | 348/74 |
| 2015/0320433 | A1* | 11/2015 | Navve .................. | A61B 17/225 |
| | | | | 606/2.5 |
| 2015/0366571 | A1* | 12/2015 | Navve ................... | A61B 5/201 |
| | | | | 606/128 |
| 2017/0215715 | A1 | 8/2017 | Harrah et al. | |
| 2019/0204068 | A1* | 7/2019 | Sonoda ............. | A61B 1/00009 |
| 2019/0204069 | A1* | 7/2019 | Tatsuta .................. | G06T 7/0012 |
| 2019/0306467 | A1* | 10/2019 | Sonoda ............... | A61B 1/0669 |
| 2019/0365200 | A1* | 12/2019 | Tatsuta ................ | A61B 5/6844 |
| 2019/0388175 | A1* | 12/2019 | Tatsuta .................... | A61B 1/06 |
| 2020/0100651 | A1* | 4/2020 | Tatsuta ............... | A61B 1/0623 |
| 2020/0149870 | A1* | 5/2020 | Thimirachandra ......................... | |
| | | | | G01B 11/2509 |
| 2021/0334941 | A1* | 10/2021 | Utsunomiya ............ | G06T 5/40 |
| 2021/0378745 | A1 | 12/2021 | Fukushima et al. | |
| 2022/0378276 | A1* | 12/2022 | Fujita ................... | A61B 5/1076 |

FOREIGN PATENT DOCUMENTS

| | | | |
|---|---|---|---|
| JP | s5867230 A | 4/1983 | |
| JP | H07136101 A * | 5/1995 | .............. G01B 9/04 |
| JP | 2005279028 A | 10/2005 | |

* cited by examiner

1/8" SPHERE AT 5mm AWAY FROM CAMERA
(IN SALINE SOLUTION)

1/8" SPHERE AT 10mm AWAY FROM CAMERA
(IN SALINE SOLUTION)

STONE MEASUREMENT SYSTEMS AND METHODS RELATED THERETO

CROSS-REFERENCE TO RELATED APPLICATIONS

This application claims the benefit of priority under 35 U.S.C. § 119 from U.S. Provisional Application No. 63/365,900, filed on Jun. 6, 2022, which is incorporated by reference herein in its entirety.

TECHNICAL FIELD

Aspects of this disclosure generally relate to medical systems and procedures. Particular aspects relate to medical systems and methods for measuring stone size and displacement of the stone from a scope.

BACKGROUND

The manner in which urinary or kidney stones may be removed from patients may depend on the size of the stones. For example, some smaller stones, or fragments of stones, may be of an adequate size to pass through a bodily lumen, e.g., the urinary tract, and out of the body. However, some larger stones, or residual fragments of stones, may require removal via an endoscopic procedure, such as retrieval by a retrieval device, e.g., a nitinol basket, grasper, etc., or further fragmentation into smaller pieces via lithotripsy. Any residual fragments greater than 5 mm may further require follow-up re-intervention to remove such fragments from a patient. Thus, accurate stone size estimation or measurement may be an important aspect of stone removal and lithotripsy.

However, obtaining accurate measurements of stone size is a known problem with existing devices. The current disclosure may solve one or more of these issues or other issues in the art.

SUMMARY

According to an example, a medical system comprises a scope including a handle and a shaft defining a channel having a distal opening; a processor; at least one laser source; a first laser fiber; and a second laser fiber, wherein each of the first laser fiber and the second laser fiber is coupled to the at least one laser source and extends through the shaft, wherein a distal end of the shaft includes an imager, the distal opening of the channel, a distal end of the first laser fiber, and a distal end of the second laser fiber, and wherein each of the first laser fiber and the second laser fiber is configured to transmit a collimated beam onto a target without altering or fragmenting the target.

In another example, the distal end of the first laser fiber and the distal end of the second laser fiber are on opposite sides of the distal opening. The first laser fiber is configured to transmit a first collimated beam and the second laser fiber is configured to transmit a second collimated beam, and the first collimated beam emitted from a distal end of the first laser fiber and the second collimated beam emitted from a distal end of the second laser fiber are parallel to each other, maintaining a distance between each other that is equivalent to a distance between a distal end of the first laser fiber and a distal end of the second laser fiber. The first laser fiber is configured to transmit a first collimated beam of a first hue, and the second laser fiber is configured to transmit a second collimated beam of a second hue, and wherein the first hue and the second hue are different.

In another example, the processor is configured to determine a depth of the target from the imager. The processor is calibrated to store a table including a series of possible pixel distances between the collimated beam of the first laser fiber and the collimated beam of the second laser fiber, and each of the possible pixel distances correlates to a possible depth of the target from the imager. The processor is configured to determine a size of the target based on a distance between the distal end of the first laser fiber, and the distal end of the second laser fiber.

In another example, the processor is configured to generate an image from imaging data obtained from the imager, and augment the image by superimposing or overlaying shapes, cues, or graphical indicators. The processor is further configured to superimpose a circle intersecting a center of the collimated beam of the first laser fiber and a center of the collimated beam of the second laser fiber.

In another example, the first laser fiber is configured to transmit a first collimated beam and the second laser fiber is configured to transmit a second collimated beam, and the processor is configured to identify a center of the first collimated beam and a center of the second collimated beam. The processor is configured to identify the center of the first collimated beam and the center of the second collimated beam via the application of a segmentation algorithm. The processor is configured to apply a hue-based threshold and/or an intensity-based threshold to identify the first collimated beam and the second collimated beam prior to the application of the segmentation algorithm.

In another example, the distance between the distal end of the first laser fiber and the distal end of the second laser fiber is approximately 1 mm to approximately 5 mm. In another example, the distance between the distal end of the first laser fiber and the distal end of the second laser fiber is approximately 3 mm. In another example, the medical system further comprises a third laser fiber, wherein the third laser fiber is coupled to the at least one laser source and extends through the shaft, and wherein the distal end of the shaft further includes a distal end of the third laser fiber.

According to an example, a method may comprise inserting a scope into a bodily orifice or lumen; positioning the scope adjacent to a stone within the bodily orifice or lumen; projecting a first collimated beam, via a first fiber of the scope, onto the stone and a second collimated beam, via a second fiber of the scope, onto the stone, wherein a distance between the first collimated beam and a second collimated beam is known; and measuring a dimension of the stone, based on the known distance between the first collimated beam and the second collimated beam. The method may further comprise comparing the measured dimension of the stone to a size threshold. The method may further comprise determining, based on the comparison between the measured dimension of the stone and the size threshold, that: 1) the stone is of an adequate size to pass through a bodily lumen; 2) the stone requires removal via an endoscopic procedure; or 3) the stone requires further fragmentation into smaller pieces via lithotripsy. The method may further comprise augmenting an image of the stone, wherein augmenting includes superimposing a circle, wherein a diameter of the circle is equivalent to a diameter of a working channel of the scope.

According to an example, a method may comprise projecting a first collimated beam, via a first fiber of the scope, onto a stone within a bodily orifice or lumen and a second collimated beam, via a second fiber of the scope, onto the stone; receiving image data about the stone, the first collimated beam, and the second collimated beam from an imager of the scope; generating from the received image data a visual representation of the stone, the first collimated beam, and the second collimated beam; determining from the visual representation, a pixel distance between the first collimated beam and the second collimated beam; and identifying a depth of the stone from the imager based on the determined pixel distance between the first collimated beam and the second collimated beam.

It may be understood that both the foregoing summary and the following detailed descriptions are exemplary and explanatory only, neither being restrictive of the inventions claimed below.

BRIEF DESCRIPTION OF THE DRAWINGS

The accompanying drawings are incorporated in and constitute a part of this specification. These drawings illustrate aspects of the disclosure that, together with the written descriptions herein, serve to explain this disclosure. Each drawing depicts one or more exemplary aspects according to this disclosure, as follows.

DETAILED DESCRIPTION

Figure 1A:
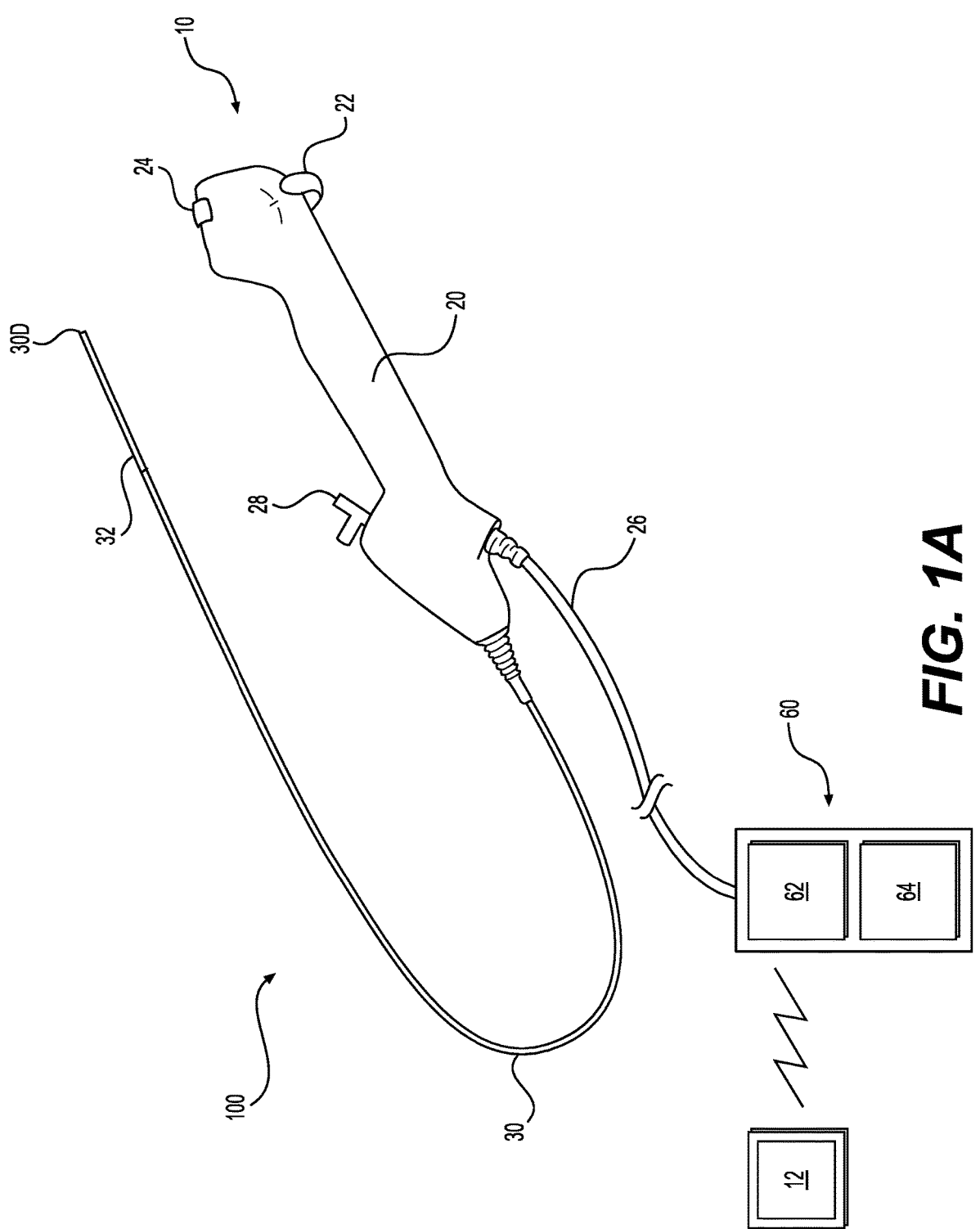
FIG. 1A depicts an exemplary scope.

In some techniques, where an imaging device is used to visualize a stone, a surgeon may manually estimate stone size by comparing an unknown dimension of the stone (e.g., a perceived maximum width) with a known dimension of a medical scope or accessory instrument, e.g., a diameter of an opening of a retrieval device. These estimations are often inaccurate, owing to the inherent challenges associated with measuring a three-dimensional object from a two-dimensional image, especially when the image is of low resolution or visibility. Because of these inaccuracies, the surgeon may be required to remove and/or further fragment more stones than medically required, increasing operation times. Even more time may be lost if the surgeon introduces a retrieval device based on the estimated stone size, then finds the fragment too big for the device, requiring removal of the retrieval device and/or further fragmentation of the stone.

In addition to accurate stone size estimation, accurate measurement of the displacement or depth of the stone from a distal tip of the medical scope may also be important for related purposes. For example, for laser lithotripsy, the displacement of the stone from the lithotripsy device (which may extend from a distal end of the medical scope) may be an important parameter when determining the degree of laser energy to be delivered to fragment the stone. However, estimation of this displacement based on the imaging provided by the scope may often be inaccurate and unreliable, which in turn may affect the delivery of laser for lithotripsy purposes. The disclosed methods and devices may produce more accurate measurements of stones than existing methods and devices.

Aspects of the disclosure are now described with reference to exemplary systems and methods for measuring stone size and displacement. Some aspects are described with reference to medical procedures where a scope is guided through a body until a distal end of the scope is located in a body cavity including one or more stone objects. For example, the scope may include an elongated sheath that is guided through a urethra, a bladder, and a ureter until a distal end of the sheath is located in a calyx of a kidney, adjacent one or more kidney stones. References to a particular type of procedure, such as medical; body cavity, such as a calyx; and stone object, such as a kidney stone, are provided for convenience and not intended to limit the disclosure unless claimed. Accordingly, the concepts described herein may be utilized for any analogous device or method—medical or otherwise, kidney-specific or not.

Wherever possible, the same or similar reference numbers will be used throughout the drawings to refer to the same or like parts. The term "distal" refers to a portion farthest away from a user when introducing a device into a subject (e.g., patient). By contrast, the term "proximal" refers to a portion closest to the user when placing the device into the subject. Unless claimed, these terms are provided for convenience and not intended to limit the disclosure to a particular location, direction, or orientation.

Both the foregoing general description and the following detailed description are exemplary and explanatory only and are not restrictive of the features, as claimed. As used herein, the terms "comprises," "comprising," "having," "including," or other variations thereof, are intended to cover a non-exclusive inclusion such that a process, method, article, or apparatus that comprises a list of elements does not include only those elements, but may include other elements not expressly listed or inherent to such a process, method, article, or apparatus. In this disclosure, relative terms, such as, for example, "about," "substantially," "generally," and "approximately" are used to indicate a possible variation of ±10% in a stated value or characteristic.

Embodiments of the disclosure may solve one or more of the limitations in the art. The scope of the disclosure, however, is defined by the attached claims and not the ability to solve a specific problem.

The disclosure is drawn to medical systems including a medical device, i.e., a scope, including at least two laser transmitters, e.g., fibers, set at a distal end of the scope, and methods for performing medical procedures using the medical device. Each of the at least two laser transmitters is configured to deliver a collimated beam, which may be projected or shone onto the targeted stone. As discussed in further detail below, such projection of the at least two collimated beams, via the scope, may be able to accurately measure the size of the stone, as well as the displacement of the stone from the distal end of the scope.

An exemplary system 100 is now described with reference to FIG. 1A. System 100 comprises a medical device, e.g., a scope 10, which may be in connection with equipment supporting the medical device, e.g., a tower 60. Tower 60 is not particularly limited. Tower 60 may be any suitable equipment, such as capital equipment, configured to be operable with scope 10, and to supply scope 10 with any necessary sources, e.g., light, vacuum/suction, fluid, air/insufflation, power, signals, etc. As shown in FIG. 1A, tower 60 further includes at least a processing unit 62, which may be operable with an imaging unit of scope 10, and help generate a visual representation of the image data, and transmit the visual representation to one or more interface devices, e.g., a screen 12. Processing unit 62 also may augment the visual representation. Screen 12 is not particularly limited and may be any suitable display, e.g., a touchscreen display, for displaying the image generated by the scope camera and processing unit 62.

Tower 60 may also include at least one laser 64. Laser 64 is not particularly limited, and may be any suitable laser device, e.g., one or more laser pointer(s), gas laser source(s), liquid laser source(s), semiconductor laser source(s), excimer laser source(s), laser diode(s), etc., as well as any suitable non-laser device, e.g., a LED with a collimator. In some examples, laser 64 may be of a small enough size so that laser 64 may be incorporated into scope 20 itself, as opposed to being in tower 60. In some examples, one laser 64 may generate a plurality (i.e., two more) beams. In other examples, each laser 64 may generate one beam, and tower 60 may include multiple lasers 64. The intensity, hue, and other aspects of the beam generated by laser(s) 64 is not particularly limited so long as the beam may be safely shone on a designated target stone, without altering, e.g., fragmenting, the target stone, as described below. In some examples, one or more lasers 64 may generate a first beam having a first color and a second beam having a second color. Laser(s) 64 may generate any suitable number of beams. All or some of the beams may have similar properties, or each of the beams may have unique properties. Laser(s) 64 may generate collimated beams, or other types of beams. Further properties of the beams from laser(s) 64 are discussed in further detail below.

Tower 60 may further include any additional equipment and/or devices that may be suitable or desired, including, e.g., monitor(s), tubing(s), cable(s), etc. (not shown). Furthermore, the manner in which tower 20 and its various sources, equipment, etc. are arranged is not particularly limited. For example, though "tower" may imply a vertical arrangement of components/equipment used for support of device 10, the arrangement of components/equipment may be in any suitable fashion, and the term "tower" is not limited to a particular arrangement.

Figure 1B:
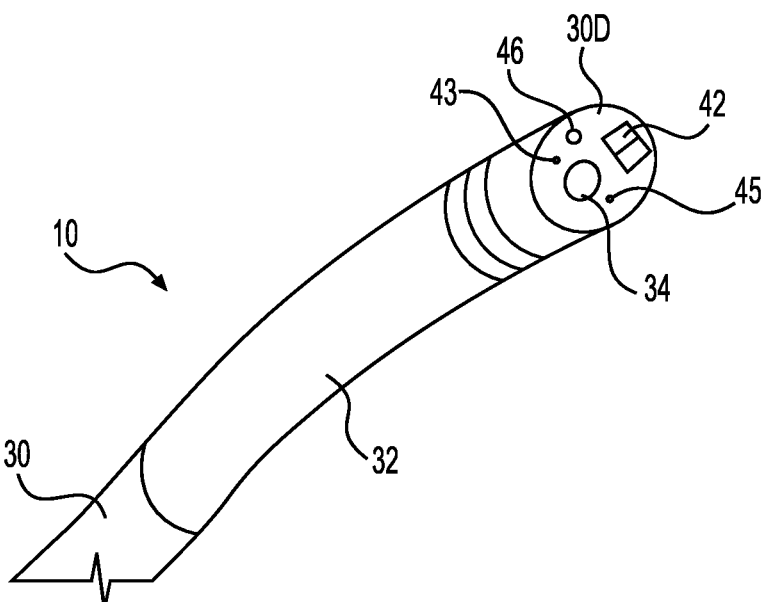
FIG. 1B depicts an exemplary distal end of the scope of FIG. 1A.
Figure 1C:
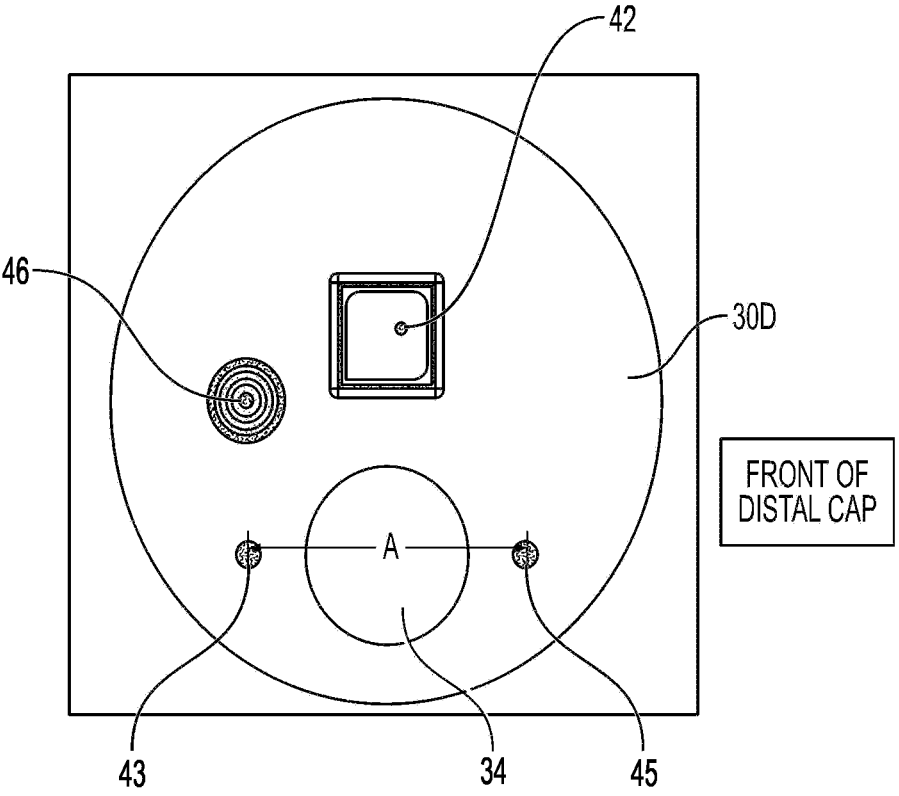
FIG. 1C depicts an exemplary distal face of the distal end shown in FIG. 1B.

Scope 10 of FIGS. 1A-C is not particularly limited, and may be, as an example, any scope (e.g., bronchoscope, duodenoscope, endoscope, colonoscope, ureteroscope, etc.), catheter, tool, instrument, or the like, having a shaft/catheter that extends distally from a handle. In this example, scope 10 comprises: a handle 20 with a first actuator 22 and a second actuator 24; a cable 26; a port 28; and an elongated shaft 30 with a steerable portion 32.

Handle 20 is also not particularly limited, and may be any suitable medical device handle. First actuator 22 is not particularly limited, and may be any suitable control that may be operable, for example, to articulate steerable portion 32 by application of forces to the pull-wires contained within shaft 30. For example, first actuator 22 may include a lever, as shown in FIG. 1A. In alternatives, first actuator may include, for example, a knob, a slider, a joystick, a button, or any other type of mechanism. Likewise, second actuator 24 is also not particularly limited, and may be operable for other suitable purposes, such as actuating or controlling other aspects of scope 10, e.g., turning on/off laser 64, performing image capture, or operating any tools or accessory instruments associated with scope 10. For example, second actuator 24 may include a button, as shown in FIG. 1A. In alternatives, first actuator may include, for example, a knob, a slider, a joystick, a lever, or any other type of mechanism.

Cable 26 (e.g., an umbilicus), as depicted in FIG. 1A, is in connection with an aspect of tower 60. For example, a proximal end of cable 26 may terminate in a connector that is configured to mate with a socket of tower 60. Cable 26 is not particularly limited, and may include any suitable wiring/sheath suitable for various purposes. For example, cable 26 may be configured to sheath various cables and wirings (not shown) that transmit imaging data to processing unit 62 from imager 42 (shown in FIGS. 1B-1C). In addition (or alternatively), cable 26 may sheath laser fibers such as a first laser fiber 43 and a second laser fiber 45. Laser fibers 43, 45 may include Holmium fibers, or other types of laser fibers or optical fibers with collimator. Each of first laser fiber 43 and second laser fiber 45 may be removably couplable to laser source(s) 64 via, for example, the connector at the proximal end of cable 26. For example, one or more of the connector of cable 26 or the socket of tower 12 may include a laser-to-fiber coupler. Such a coupler is not particularly limited, and may include any soldering or intermediary lenses which may assist with the coupling between fibers 43, 45 and laser source 64. First laser fiber 43 and second laser fiber 45 (shown in FIGS. 1B and 1C), may each be configured to transmit a collimated beam (or other type of beam) from laser source 64 to distal ends of first laser fiber 43 and second laser fiber 45, respectively. As discussed in further detail below, first laser fiber 43 and second laser fiber 45 may extend through handle 20, towards a distal end 30D of shaft 30. Although two laser fibers 43, 45 are depicted in FIGS. 1B and 1C, it will be appreciated that any suitable number of laser fibers may be utilized. For example, three, four, five, or more laser fibers may be utilized. In at least some examples, it may be advantageous to include two or more laser fibers 43, 45.

As shown in FIG. 1A, port 28 may be mounted on a distal portion of handle 20, and include openings in communication with a working channel 34 (shown in FIGS. 1B-1C) of elongated shaft 30, discussed below. Any suitable accessory instrument/device or elongated tool, e.g., lithotripsy device, grasper, retrieval device, etc., may be inserted through port 28, and moved distally through the distal portion of handle 20 and/or working channel 34.

As shown in FIGS. 1A-B, elongated shaft 30 extends distally from handle 20 before terminating at distal end 30D of shaft 30. Shaft 30 is not particularly limited, and may be any suitable flexible shaft configured to traverse bodily lumens during a procedure. As noted above, shaft 30 may include a steerable/articulating portion 32 that is adjacent to distal end 30D. Portion 32 is not particularly limited, and may be any standard articulating portion of medical scope shafts.

Shaft 12 may further include at least one working channel 34, which may extend longitudinally from port 28 of handle 20 to distal end 30D of shaft 30. Shaft 30 may also include at least one lumen(s) for receiving any number of additional wirings, cables, and/or fibers from tower 60 that support the various features present on distal end 30D of shaft 30, which are discussed in further detail below. Laser fibers 43, 45 may extend from cable 26, through an interior of handle 20, and through shaft 30. For example, laser fibers 43, 45 may extend through lumen(s) of shaft 30 or through a central opening defined by an outer sheath of shaft 30. For example, each of first laser fiber 43 and second laser fiber 45 may include a single, continuous, monolithic piece of fiber extending from the connector of cable 26 to distal end 30D. In alternatives, one or both of first laser fiber 43 and second laser fiber 45 may include multiple pieces that are in optical communication with one another (e.g., joined by connectors or fused together).

As shown in FIGS. 1B and 1C, distal end 30D of shaft 30 may include at least a distal opening of working channel 34, imager 42, a light 46, and distal ends of laser fibers 43, 45. In other examples, shaft 30 may further include a distal cap (not shown) covering portions of distal end 30D, thereby protecting features such as imager 42, light 46, and laser fibers 43, 45.

The distal opening of working channel 34 is not particularly limited, and may be of any suitable width to enable the extension/retraction of an instrument or tool within/out of working channel 34. Imager 42 is also not particularly limited, and may be any suitable device configured to receive imaging data, (e.g., via any sensor), of a designated target, such as, e.g., a stone, and transmit the imaging data to an image processor, such as, e.g., processing unit 62, for producing a visual representation of the imaging data. In some examples, imager 42 may be a camera including a CMOS sensor. In other examples, imager 42 may include fiber optics in communication with a sensor or other device that may be positioned within shaft 30 or handle 20. However, imager 42 is not limited to the aforementioned examples. Light 46 is also not particularly limited and may be any suitable device configured to provide a source of light, particularly when shaft 30 is traversing bodily lumens and imager 42 is capturing imaging data of a designated target. In some examples, light 46 may include a plastic optical fiber ("POF") device configured to provide light from a light source of tower 12, such as, e.g., an LED, or an LED mounted at distal end 30D.

As shown in FIGS. 1B and 1C, the distal tips/ends of first laser fiber 43 and second laser fiber 45 may be present on distal end 30D of shaft 30. As discussed above, while two laser fibers are depicted in shaft 30, the number of laser fibers is not particularly limited so long as there is available space within shaft 30/on distal end 30D to accommodate the additional laser fibers. In some examples, system 100 may further include a third laser fiber, a fourth laser fiber, etc. As discussed above, laser fibers 43 and 45 are not particularly limited, and may be any suitable fiber for laser transmission. As discussed above, fibers 43 and 45 may be in communication with laser source 64 of tower 60. Laser source(s) 64 may transmit or project a collimated beam, which may travel through fibers 43, 45. Fibers 43 and 45 may be on diametrically opposite sides of the distal opening of working channel 34. For example, fibers 43 and 45 may each be adjacent to the distal opening of working channel 34, on diametrically opposite sides of the distal opening of working channel 34. A line drawn through fibers 43 and 45 may approximately intersect a central axis of the distal opening of working channel 34. However, the position of fibers 43 and 45 on distal end 30D is not limited thereto.

A distance or displacement between a center of fiber 43 and a center of fiber 45, distance A as shown in FIG. 1C, may be pre-defined. For example, shaft 30 may be configured such that the displacement between fiber 43 and fiber 45 may be any pre-defined distance A, e.g., 1 mm, 2 mm, 3 mm, 4 mm, 5 mm, 6 mm, 7 mm, etc. If additional fibers are utilized, distal ends of the fibers may be positioned in any suitable way. For example, the distal ends of the fibers may be positioned about the distal opening of working channel 34. A distance between each of the fibers may be equal (e.g., distance A) or may vary. Fibers 43 and 45 may transmit parallel, collimated beams, having a consistent distance A between the beams regardless of the distance the collimated beams are transmitted.

Figure 2A:
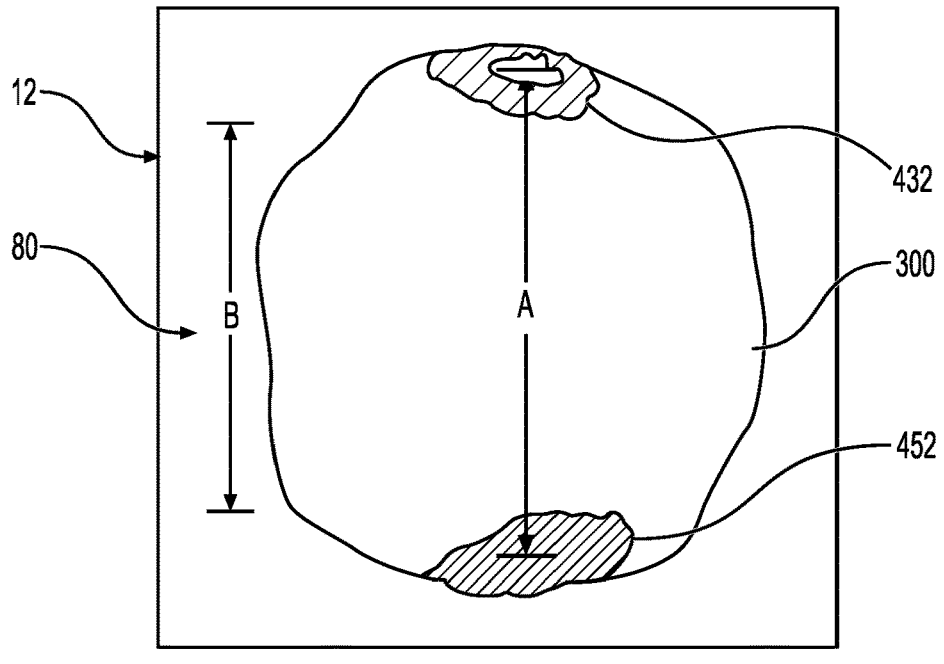
FIGS. 2A-2B depict exemplary images obtained from the scope of FIG. 1A.

This consistent, pre-determined distance A between the center of first laser fiber 43 and the center of second laser fiber 45 may be used to accurately measure, or estimate, a size of a targeted stone. An example of this process is illustrated in FIG. 2A. FIG. 2A illustrates an exemplary image 80, captured via imager 42, which may be displayed on a screen 12. In generating image 80, distal end 30D (and thus imager 42) of scope 10 is positioned adjacent to, e.g., approximately 5 mm away from a target stone 300, which may be of an approximately spherical shape having approximately a ⅛" inch diameter. A first collimated beam 432 is transmitted onto stone 300 via first laser fiber 43 and a second collimated beam 452 is transmitted onto stone 300 via second laser fiber 45. First collimated beam 432 and second collimated beam 452 may be transmitted onto stone 300 so that beams 432, 452 may be along a dimension of stone 300, e.g., a major axis of stone 300. The center of first collimated beam 432 and the center of second collimated beam 452 are separated by distance A, e.g., 3 mm, approximately equal to the separation between first laser fiber 43 and second laser fiber 45 on distal end 30D. Thus, given that distance A is known to a user, tower 12, and/or another element of system 100, and distance A, i.e., 3 mm, is approximately equivalent to a diameter of target stone 300 in the view of FIG. 3A, i.e., ⅛" inch (or 3.175 mm), an approximately accurate assessment/estimation of the size of stone 300 may be made to determine the manner in which the stone may be removed or whether lithotripsy is needed. For example, processing unit 62 of tower 12 or another aspect of system 100, or user of system 100, may estimate a size of stone 300 based on known distance A. The user or processing unit 62 may subsequently compare the size of stone 300 to a preset size threshold or thresholds. Based on such comparison, the user or processing unit 62 may determine, for example, that the stone is of an adequate size to pass through a bodily lumen, requires removal via an endoscopic procedure, or requires further fragmentation into smaller pieces via lithotripsy. An exemplary process by which processing unit 62 may determine the size of stone 300 may include implementing any suitable image segmentation technique/algorithm to determine a pixel distance of a major axis of stone 300 and a pixel distance of distance A, which may be along the major axis of stone 300, and calculating a ratio between a pixel distance of the major axis of stone 300 and a pixel distance A. For example, a major axis of stone 300 in image 80 may be 300 pixels, while distance A may be 200 pixels in image 80. In this example, the actual physical distance of distance A may be 3 mm, which is equivalent to the separation between first laser fiber 43 and second laser fiber 45 on distal end 30D. Thus, processing unit 62 may calculate the size of stone 300 by multiplying the aforementioned pixel distance ratio between the major axis of stone 300 and distance A with the actual physical distance of distance A, i.e., $$\frac{300 \text{ pixel distance}}{200 \text{ pixel distance}} * 3 \text{ mm} = 4.5 \text{ mm}.$$

Identifying a center of the collimated beams for various purposes, e.g., determining a pixel distance of distance A, is further discussed below when discussing FIGS. 4A-4C.

Figure 2B:
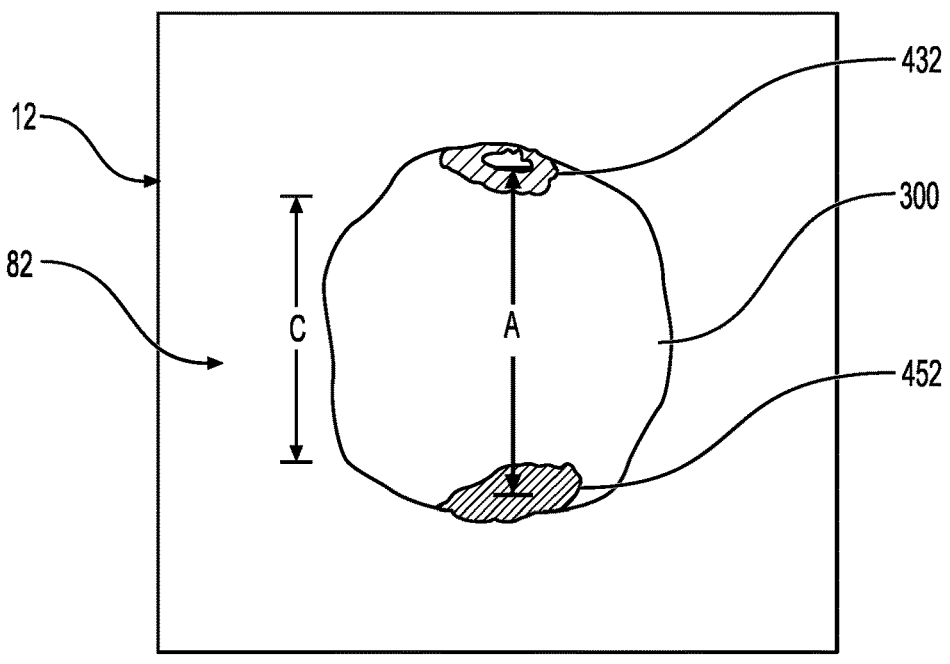

It is noted that, in an image, e.g., image 82 of FIG. 2B, beams 432 and 452 of fibers 43 and 45, respectively, may disperse as distal end 30D moves further away from stone 300 onto which beams 432 and 452 are projected. However, the actual distance between the centers of beams 432 and 452 consistently remains distance A, due to beams 432 and 452 being collimated. Thus, scope 10 may be adjusted relative to stone 300 until beams 432 and 452 are positioned on either side of stone 300, as shown in FIGS. 2A and 2B, or along any aspect or dimension of stone 300 that is to be measured.

Furthermore, in other examples in which the width of stone 300 significantly exceeds pre-determined distance A, the user may re-position scope 10 repeatedly so that collimated beams 432 and 452 are traced across a dimension of stone 300, e.g., the width of stone 300, thereby measuring the width like one would with typical measuring instruments. For example, when a width or diameter of stone 300 is approximately double of distance A, a user may first position scope 10 so that a center of beam 432 aligns, or approximately aligns, with a center of stone 300, and a center of beam 452 aligns, or approximately aligns, with a first point along an edge of stone 300. The user may subsequently re-position scope 10 so that a center of beam 452 aligns, or approximately aligns, with the center of stone 300, and that a center of beam 432 aligns, or approximately aligns, with a second point along an aspect of stone 300) that is diametrically opposite of the first point. The user may repeat such re-positioning and measuring until an approximately accurate assessment/estimation of the size of stone 300 may be made based on the known distance of distance A and the number of re-positioning that was needed to measure the size of stone 300.

FIG. 2B illustrates another exemplary image 82, captured via imager 42, and displayed on a screen 12. In image 82, distal end 30D (and thus imager 42) of scope 10 is positioned adjacent to, e.g., approximately 10 mm away from target stone 300. Despite the additional displacement between distal end 30D and stone 300, relative to that shown in image 80, the distance between beams 432 and 452 remains the same distance A given the collimated nature of the beams.

However, as shown in FIGS. 2A and 2B, a pixel distance between first collimated beam 432 and second collimated beam 452 in image 80, i.e., distance B, and the pixel distance between first collimated beam 432 and second collimated beam 452 in image 82, i.e., distance C, vary from one another. Processing unit 62 may measure pixel distance via any suitable means. This difference between distance B and distance C may be attributed to the difference in displacement or depth of stone 300 from distal end 30D of scope 10. This difference in pixel distance may be utilized to also measure or estimate the depth of stone 300 from distal end 30D of scope 10. For example, the pixel distance between at least two beams, e.g., beam 432 and beam 452, within an image, e.g., image 80 or image 82, may be calibrated to a depth of stone 300 from imager 42 (and thus, distal end 30D of scope 10). Such calibration may be via any suitable manner—for example, a table, e.g., a look-up table, may be created and stored within processing unit 62, and the table may include a series of pixel distances, each pixel distance correlating to a specific depth of an imaged target from imager 42, e.g., 1 pixel—20 mm, 2 pixels—10 mm, 3 pixels—6 mm, 5 pixels—4 mm, 10 pixels—3 mm, 20 pixels—2 mm, 100 pixels—0.5 mm, etc. This look-up table may be created during a calibration process, e.g., in a lab setup with externally measured depth information. Thus, a user or processing unit 62 may identify a pixel distance, e.g., distance B or distance C, between first collimated beam 432 and second collimated beam 452, and subsequently identify the depth that correlates to the aforementioned pixel distance, based on the table. Thus, scope 10 may be utilized to measure a size of stone 300 and also the depth of stone 300 from distal end 30D of scope 10.

Figure 3:
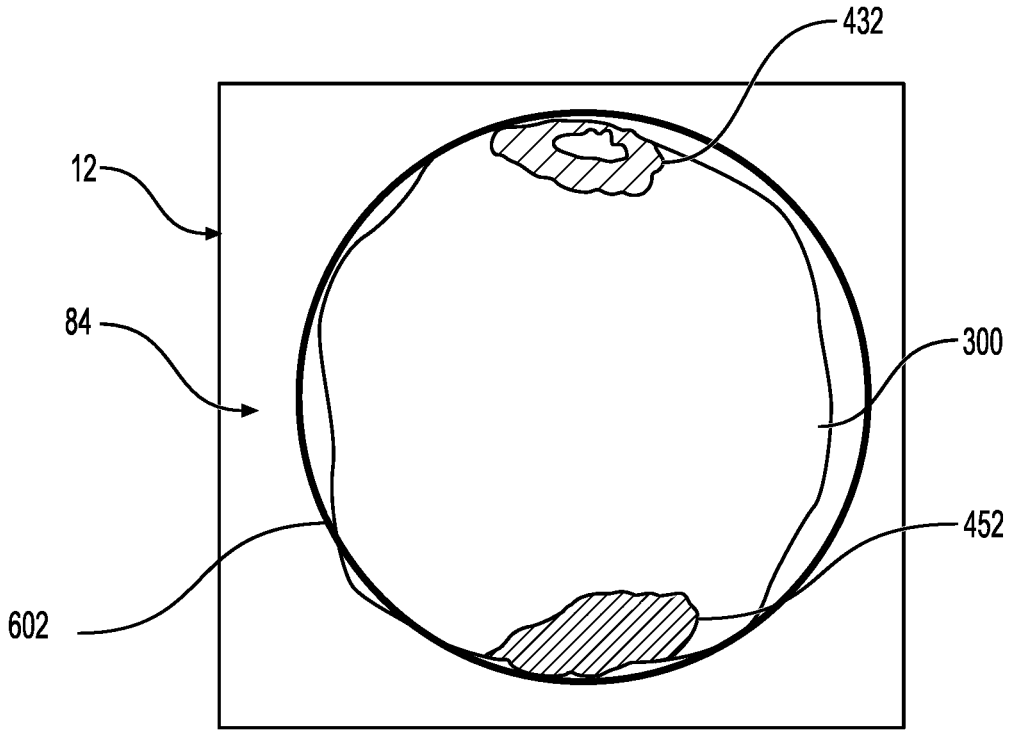
FIG. 3 depicts an exemplary augmented image obtained from the scope of FIG. 1A.

As shown in FIG. 3, image 84, including stone 300, first collimated beam 432, and second collimated beam 452, may be augmented. The manner by which image 84 may be augmented is not particularly limited. For example, augmentation of image 84 may include: transmitting to processing unit 62, from imager 42, image data of stone 300 and a surrounding body lumen or cavity; generating from the image data, with processing unit 62, a visual representation of stone 300 and the surrounding body lumen or cavity; and augmenting the visual representation by superimposing or overlaying shapes, e.g., a circle 602, graphical cues, graphical indicators, etc., thereby producing image 84. In some examples, image 84 may be a real-time, live visual representation of stone 300 and the surrounding body lumen or cavity, and augmentation may be applied to the live visual representation.

In some examples, the above-described augmentation of image 84 may be utilized for stone size measuring/assessment purposes. For example, circle 602 may be superimposed/overlayed onto image 84, via a processor as discussed above. Circle 602 may be of a known diameter, e.g., 1 mm, 5 mm, or the diameter of the distal opening of working channel 34, so a user, or processing unit 62, may cross-reference the size of stone 300 to the diameter of circle 602, and, for example, determine whether stone 300 may be captured and removed via working channel 34, or whether fragmentation of stone 300 is necessary. Processing unit 62 may overlay circle 602 by first determining a pixel distance that corresponds to the actual physical diameter of the distal opening of working channel 34. The pixel distance may be determined by the known distance of distance A, and the known diameter of the distal opening of working channel 34. For example, processing unit 62 may recognize that distance A is, for example, 3 mm, the access sheath is, for example, a diameter of 4 mm, and thus, determine that the size, i.e., the pixel distance, of circle 602 is to be 4/3 of the pixel distance of distance A in image 84.

Figure 4A:
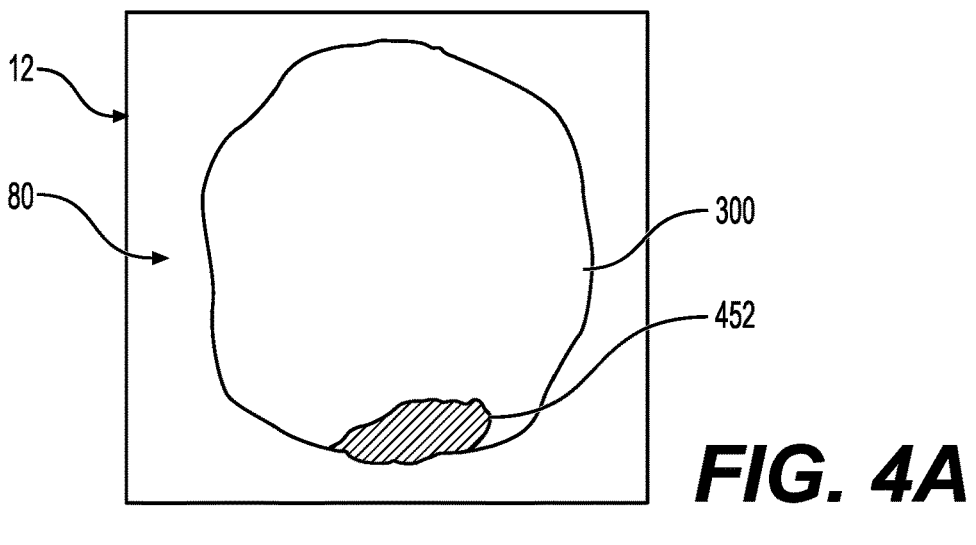
FIGS. 4A-4C depict an exemplary process of augmenting an image from the scope of FIG. 1A.
Figure 4B:
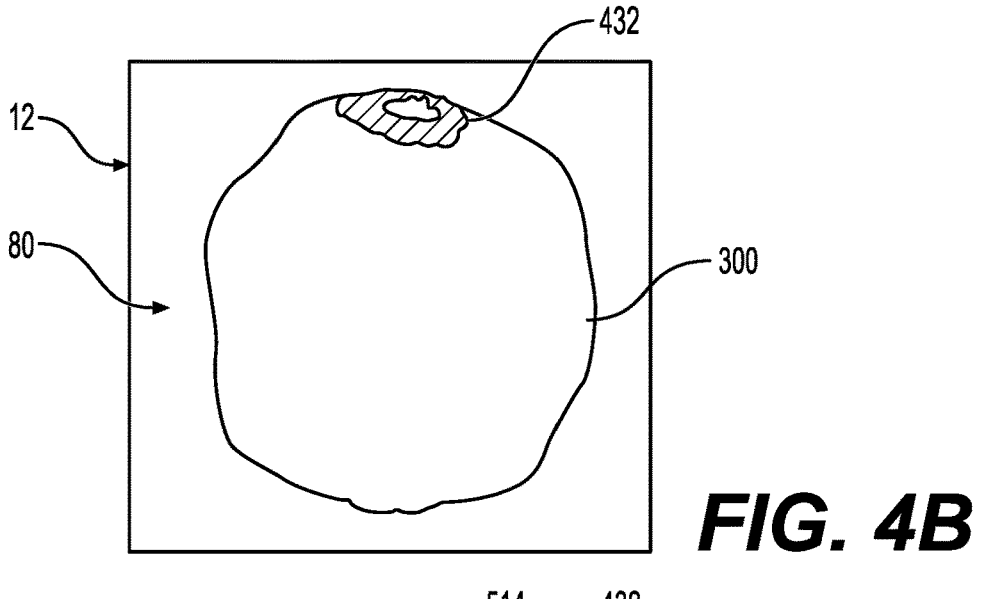
Figure 4C:
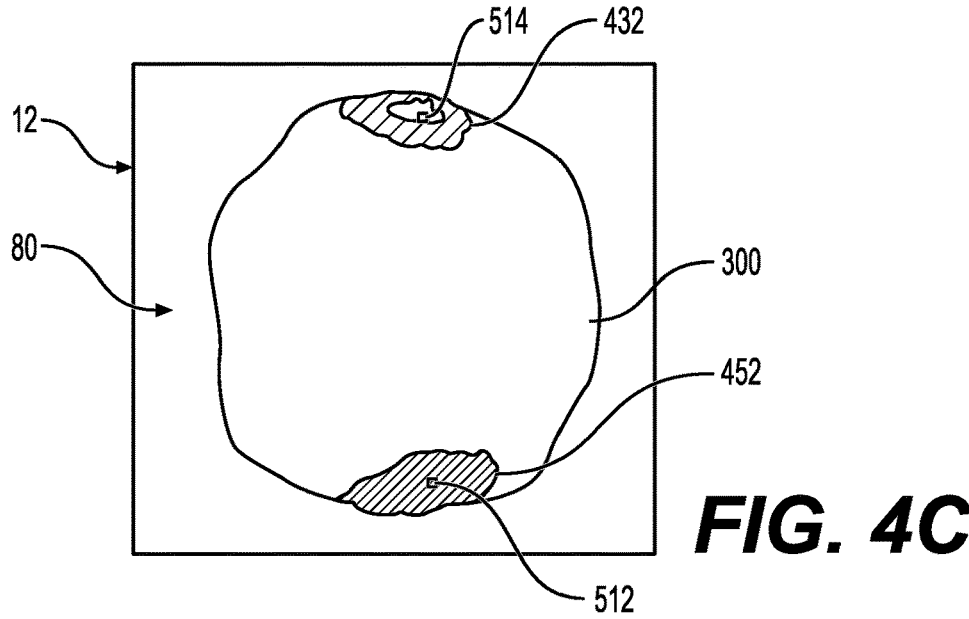

FIGS. 4A-4C illustrate an exemplary process by which the center of first collimated beam 432 and the center of second collimated beam 452 may be determined. In some examples, first collimated beam 432 and second collimated beam 452 may vary in color/hue, e.g., a red beam 432 vs. a green beam 452. In view of such a difference, processing unit 62 may apply a hue-based threshold, e.g. a red hue-based threshold, to identify first collimated beam 432, as shown in FIG. 4A. Segmentation may be applied thereafter to collimated beam 432 via processing unit 62. The manner in which beam 432 is segmented is not particularly limited, and may be via any suitable image segmentation algorithm. Processing unit 62 may subsequently apply a second hue-based threshold, e.g., a green hue-based threshold, to identify second collimated beam 452, as shown in FIG. 4B. Segmentation may be applied thereafter to collimated beam 452 via processing unit 62. The manner in which beam 452 is segmented is also not particularly limited, and may be via any suitable image segmentation algorithm. It is noted that additional image processing techniques, e.g., intensity-based thresholds, may also be implemented to assist the aforementioned segmentation process. After segmentation of both beam 432 and beam 452, the centers of beam 432 and 452 may be determined via any suitable manner, e.g., a center of mass calculation. Given that each pixel in segmented beam 432 and segmented beam 452 has a (x,y) coordinate, processing unit 62 may obtain all the coordinates of segmented beams 432, 452 to calculate the center of the segmented beams. An exemplary center of mass calculation may be:

US 12,678,257 B2

11

$$X_c = \left(\sum_{i=1}^{N} X\_i\right)/N,\ Y_c = \left(\sum_{i=1}^{N} Y\_i\right)/N,\ \text{where}\ (X_c, Y_c)$$

is the center of the laser dot, and N is the total pixel number in segmented beam 432 or beam 452.

While principles of the disclosure are described herein with reference to illustrative aspects for particular applications, the disclosure is not limited thereto. Those having ordinary skill in the art and access to the teachings provided herein will recognize additional modifications, applications, aspects, and substitution of equivalents all fall in the scope of the aspects described herein. Accordingly, the disclosure is not to be considered as limited by the foregoing description.

What is claimed is:

1. A medical system comprising:
a scope including a handle and a shaft defining a channel having a distal opening;
a processor;
at least one laser source;
a first laser fiber; and
a second laser fiber, wherein each of the first laser fiber and the second laser fiber is coupled to the at least one laser source and extends through the shaft;
wherein a distal end of the shaft includes an imager, the distal opening of the channel, a distal end of the first laser fiber, and a distal end of the second laser fiber;
wherein each of the first laser fiber and the second laser fiber is configured to transmit a collimated beam onto a target without altering or fragmenting the target; and
wherein the processor is configured to:
determine a size of the target based on at least a distance between a distal end of the first laser fiber and a distal end of the second laser fiber, a pixel distance between a first collimated beam emitted from the distal end of the first laser fiber and a second collimated beam emitted from the distal end of the second laser fiber, and a pixel distance of a dimension of the target;
generate an image from imaging data obtained from the imager; and
augment the image by superimposing or overlaying shapes, cues, or graphical indicators, wherein the superimposing comprises augmenting the image with a circle intersecting a center of the first collimated beam of the first laser fiber and a center of the second collimated beam of the second laser fiber.

2. The medical system of claim 1, wherein the distal end of the first laser fiber and the distal end of the second laser fiber are on opposite sides of the distal opening.

3. The medical system of claim 1, wherein the first collimated beam and the second collimated beam are parallel to each other, maintaining a distance between each other that is equivalent to the distance between the distal end of the first laser fiber and the distal end of the second laser fiber.

4. The medical system of claim 1, wherein the first laser fiber is configured to transmit the first collimated beam of a first hue, and the second laser fiber is configured to transmit the second collimated beam of a second hue, and wherein the first hue and the second hue are different.

5. The medical system of claim 1, wherein the processor is further configured to determine a depth of the target from the imager.

6. The medical system of claim 5, wherein the processor is calibrated to store a table including a series of possible pixel distances between the collimated beam of the first laser fiber and the collimated beam of the second laser fiber, and each of the possible pixel distances correlates to a possible depth of the target from the imager.

7. The medical system of claim 1, wherein the processor is further configured to identify a center of the first collimated beam and a center of the second collimated beam.

8. The medical system of claim 7, wherein the processor is configured to identify the center of the first collimated beam and the center of the second collimated beam via application of a segmentation algorithm.

9. The medical system of claim 8, wherein the processor is further configured to apply a hue-based threshold and/or an intensity-based threshold to identify the first collimated beam and the second collimated beam prior to the application of the segmentation algorithm.

10. The medical system of claim 1, wherein the distance between the distal end of the first laser fiber and the distal end of the second laser fiber is approximately 1 mm to approximately 5 mm.

11. The medical system of claim 1, wherein the distance between the distal end of the first laser fiber and the distal end of the second laser fiber is approximately 3 mm.

12. The medical system of claim 1, wherein the processor is further configured to determine the size of the target by:
calculating a ratio between the pixel distance of the dimension of the target and the pixel distance between the first collimated beam and the second collimated beam; and
multiplying the ratio by the distance between the distal end of the first laser fiber and the distal end of the second laser fiber.

13. A method, comprising:
inserting a scope into a bodily orifice or lumen;
positioning the scope adjacent to a stone within the bodily orifice or lumen;
projecting a first collimated beam having a first hue, via a first fiber of the scope, onto the stone and projecting a second collimated beam having a second hue, via a second fiber of the scope, onto the stone, wherein a distance between the first collimated beam and a second collimated beam is known;
identifying the first collimated beam by applying a first hue-based threshold to an image captured by an imager of the scope;
identifying the second collimated beam by applying a second hue-based threshold to the image; and
measuring a dimension of the stone, based on the known distance between the first collimated beam and the second collimated beam.

14. The method of claim 13, further comprising comparing the measured dimension of the stone to a size threshold.

15. The method of claim 14, further comprising determining, based on the comparison between the measured dimension of the stone and the size threshold, that:
1) The stone is of an adequate size to pass through a bodily lumen;
2) The stone requires removal via an endoscopic procedure; or
3) The stone requires further fragmentation into smaller pieces via lithotripsy.

16. The method of claim 13, further comprising augmenting an image of the stone, wherein augmenting includes superimposing a circle, wherein a diameter of the circle is equivalent to a diameter of a working channel of the scope.

17. A method comprising:

projecting a first collimated beam having a first hue, via a first fiber of a scope, onto a stone within a bodily orifice or lumen and projecting a second collimated beam having a second hue, via a second fiber of the scope, onto the stone;

receiving image data about the stone, the first collimated beam, and the second collimated beam from an imager of the scope;

generating from the received image data a visual representation of the stone, the first collimated beam, and the second collimated beam;

identifying the first collimated beam in the received image data by applying a first hue-based threshold to the received image data;

identifying the second collimated beam in the received image data by applying a second hue-based threshold to the received image data;

determining from the visual representation, a pixel distance between the first collimated beam and the second collimated beam; and identifying a depth of the stone from the imager based on the determined pixel distance between the first collimated beam and the second collimated beam.

* * * * *